US009839797B2

(12) United States Patent
Falkowski et al.

(10) Patent No.: US 9,839,797 B2
(45) Date of Patent: Dec. 12, 2017

(54) METHOD FOR PRODUCING HYDROCARBONS

(75) Inventors: Jürgen Falkowski, Monheim (DE); Markus Dierker, Düsseldorf (DE); Michael Neuβ, Köln (DE); Karl Heinz Schmid, Mettmann (DE); Stephan Würkert, München (DE); Lars Zander, Rommerskirchen (DE)

(73) Assignee: Cognis IP Management GmbH, Düsseldorf (DE)

( * ) Notice: Subject to any disclaimer, the term of this patent is extended or adjusted under 35 U.S.C. 154(b) by 1460 days.

(21) Appl. No.: 12/097,064

(22) PCT Filed: Dec. 5, 2006

(86) PCT No.: PCT/EP2006/011647
§ 371 (c)(1),
(2), (4) Date: Jun. 12, 2008

(87) PCT Pub. No.: WO2007/068371
PCT Pub. Date: Jun. 21, 2007

(65) Prior Publication Data
US 2008/0269352 A1   Oct. 30, 2008

(30) Foreign Application Priority Data
Dec. 14, 2005   (EP) .................................... 05027253

(51) Int. Cl.
| C07C 1/20 | (2006.01) |
| A61Q 19/00 | (2006.01) |
| A61K 8/31 | (2006.01) |
| A61Q 5/06 | (2006.01) |
| A61Q 17/04 | (2006.01) |

(52) U.S. Cl.
CPC ................ *A61Q 19/00* (2013.01); *A61K 8/31* (2013.01); *C07C 1/20* (2013.01); *A61Q 5/06* (2013.01); *A61Q 17/04* (2013.01); *C07C 2523/755* (2013.01)

(58) Field of Classification Search
CPC ........ C07C 1/20; C07C 9/15; C07C 2523/755
USPC ................................................. 585/733, 752
See application file for complete search history.

(56) References Cited

U.S. PATENT DOCUMENTS

| 2,753,380 A | * | 7/1956 | Pines et al. .................... 585/317 |
| 3,426,080 A | * | 2/1969 | Tummes et al. .............. 568/817 |
| 3,501,546 A | * | 3/1970 | Dubeck et al. ................ 585/733 |
| 3,920,766 A | * | 11/1975 | Jubin et al. .................... 585/733 |
| 2005/0171386 A1 | * | 8/2005 | Thampi et al. ............... 568/347 |

FOREIGN PATENT DOCUMENTS

| GB | 543327 | 2/1942 |
| GB | 1051826 | 12/1966 |

OTHER PUBLICATIONS

Pines, et al., "Dehydroxymethylation of Primary Alcohols" in J. Am. Chem. Soc, 76, 771-772, (1954).*
Schneider, et al., "Skin Cosmetics" in Ullmann's Encyclopedia of Industrial Chemistry, Wiley-VCH, available on-line Jan. 15, 2001.*
Lide, et al., CRC Handbook of Chemistry and Physics, 91st edition, 2011 Internet edition, D.R. Lide, ed.*
Wojcik, et al., "Hydrogenolysis of Alcohols to Hydrocarbons" in J. Am. Chem. Soc, 55, 1293-1294, 1933.*
Covert, et al. "Nickel by the Raney Process as a Catalyst of Hydrogenation" in J. Am. Chem. Soc, 54, 4116-4117, 1932.*
Barel, A., et al. "Handbook of Cosmetic Science and Technology," Marcel Dekker Inc. (2001). (Too Voluminous).
Pines, H., et al., "Hydrogenolysis of Alcohols," *J. of Catalysis*, vol. 17, pp. 375-383 (1970).
Maier, W. F., et al., "Direction Reduction of Alcohols to Hydrocarbons," *Zeitschrift fur Naturforschung*, Part B, 1982, pp. 392-394.
Badin, E., "Catalytic Dehydrogenation I. Catalytic Conversion of Alcohols into Aldehydes, Paraffins and Olefins," *J. of the American Chemical Society*, vol. 65, No. 10, 1943, pp. 1809-1813.
3rd Party Observation from the EP case in German, 1-5—Jan. 2011.
3rd Party Observation translated into English, 2 pgs,—Jul. 2011.

* cited by examiner

*Primary Examiner* — Sharon Pregler
(74) *Attorney, Agent, or Firm* — Marshall, Gerstein & Borun LLP

(57) ABSTRACT

A process is provided for the production of linear saturated alkanes from one or more primary alcohols, wherein the carbon chain of the one or more primary alcohols has one carbon atom more than the alkane, including conducting reductive dehydroxymethylation of one or more primary fatty alcohols containing 8 to 24 carbon atoms, at a temperature ranging from 100 to 300° C. and pressures from 1 to 250 bar in the presence of hydrogen and a catalyst, and removing water formed during the reaction.

18 Claims, No Drawings

METHOD FOR PRODUCING HYDROCARBONS

CROSS-REFERENCE TO RELATED APPLICATIONS

This application is the national phase under 35 U.S.C. §371 of PCT International Application No. PCT/EP2006/011647 which has an International filing date of Dec. 5, 2006, which designated the United States of America and which claims priority on European Patent Application number EP 05027253.3, filed Dec. 14, 2005, the entire contents of each of which are hereby incorporated herein by reference.

BACKGROUND OF THE INVENTION

Field of the Invention

This invention relates generally to a process for the production of hydrocarbons from fatty alcohols and to the incorporation of the hydrocarbons in cosmetic preparations, and more particularly, to a process for the production of linear saturated alkanes from one or more primary fatty alcohols, wherein the carbon chain of the one or more primary alcohols has one carbon atom more than the alkanes.

Background Information

Readily volatile oil components, also known as light emollients, are used in a number of formulations by the cosmetics industry. Large quantities of readily volatile components are used, in particular, for decorative cosmetics and in care formulations. These components may be, for example, volatile cyclic silicones (for example, cyclopentasiloxane or cyclomethicone) or hydrocarbons from petrochemical processes. The hydrocarbons, because of their production, are predominantly mixtures of linear and branched hydrocarbons of which the flash point can be well below 50° C. (as in the case of isododecane, for example). Examples and application-related descriptions of such formulations can be found in standard works, such as for example: "Handbook of Cosmetic Science and Technology", A Barel, M. Paye, H. Maibach, Marcel Dekker Inc. 2001. However, for toxicological and safety reasons, there will be a demand in the future for alternative raw materials for such formulations.

SUMMARY OF THE INVENTION

Briefly described, according to an aspect of the invention, a process for the production of linear saturated alkanes from one or more primary alcohols, where the carbon chain of the one or more primary alcohols has one carbon atom more than the alkane includes: conducting reductive dehydroxymethylation of one or more primary fatty alcohols containing 8 to 24 carbon atoms, at a temperature ranging from 100 to 300° C. and pressures from 1 to 250 bar in the presence of hydrogen and a catalyst; and removing water formed during the reaction.

DETAILED DESCRIPTION OF THE INVENTION

The problem addressed by the present invention was to provide alternative raw materials which, on the one hand, would be ecologically and toxicologically safe and which, on the other hand, could be directly exchanged in typical cosmetic formulations without any performance-related restrictions.

It has now been found that hydroxyl compounds, such as fatty alcohols for example, can be converted with high selectivity into pure hydrocarbons with a chain length shortened by one carbon atom by a specially conducted reaction.

Accordingly, the present invention relates firstly to a process for the production of linear saturated alkanes from primary alcohols whose carbon chain contains one carbon atom more than the alkane by dehydroxymethylation of the primary alcohols at temperatures of 100 to 300° C. and pressures of 1 to 250 bar in the presence of hydrogen and a catalyst, water being removed during the reaction, characterized in that fatty alcohols containing 8 to 24 carbon atoms are used as the primary alcohols.

The reaction involved is known as dehydroxymethylation and also as reductive dehydroxymethylation. This reaction is known per se for organic primary alcohols. It is known from the Article by Hermann Pines and T. P. Kobylinski entitled: "Hydrogenolysis of Alcohols" in Journal of Catalysis 17, 375-83 (1970) that neopentyl alcohol inter alia can be converted into isobutane. The reaction of butanol to propane in the presence of nickel catalysts in a hydrogen atmosphere is also described. However, the use of long-chain fatty alcohols for such reactions is not mentioned. In addition, the reactions described in the Article in question are not carried out on an industrial scale, but only on a "micro" scale. Although the reductive demethylation of primary organic alcohols is also described in the Article by W. F. Maier, I. This and P. Schleyer entitled: "Direction Reduction of Alcohols to Hydrocarbons" in Zeitschrift für Naturforschung, Part B, 1982, 37B(3), no long-chain fatty alcohols are disclosed or suggested as suitable educts. UK 1,051,826 describes the reductive demethylation of diols with nickel catalysts in a hydrogen atmosphere. The catalytic dehydrogenation of fatty alcohols is described by Elmer J. Badin in an Article entitled: "Catalytic Dehydrogenation I. Catalytic Conversion of Alcohols into Aldehydes, Paraffins and Olefins" in Journal of the American Chemical Society, Vol. 65, No. 10, 1943, pp. 1809-1813. The process in question is carried out at normal pressure and gives only poor yields of paraffins.

High-purity hydrocarbons with a particular chain length can be produced from the reaction mixtures obtained in accordance with the invention, preferably after purification of the crude products, for example, after fractional distillation, and—again preferably—deodorization. The hydrocarbons with a particular chain length thus obtained may either be used as individual components in cosmetic formulations as so-called light emollients or may be mixed in a particular manner in order to be able to establish special properties such as, for example, spreading behavior, volatility or even a flash point.

The hydroxyl-containing components may be fatty alcohols with the chain length mentioned above which may be produced in known manner from renewable raw materials, such as coconut oil, palm oil or palm kernel oil for example, by transesterification with methanol and subsequent hydrogenation. Besides pure fatty alcohols, other linear or branched, monohydric or polyhydric alcohols, alcohol mixtures or derivatized alcohols produced on an industrial scale may also be used in principle and are preferred. The use of fatty alcohols with even-numbered carbon chains is particularly preferred because the odd-numbered alkanes otherwise so difficult to produce can readily be obtained in this way. In a preferred embodiment, the primary alcohols used correspond to the general formula R—OH, where R is a saturated linear alkyl group containing 8 to 18 carbon atoms, preferably 10 to 16 carbon atoms and more particularly 12 to 16 carbon atoms.

The reaction of the alcohols to the hydrocarbons must be carried out in the presence of hydrogen and must be accompanied by the removal of water.

Particularly suitable catalysts are platinum, rubidium or nickel-containing catalysts. However, nickel catalysts are preferably used, more particularly commercially available Ni-containing hydrogenation catalysts such as, for example, the catalysts available from Engelhard or Kata Leuna. The catalysts may be used both as suspension catalysts for a semi-batch process and as fixed-bed catalysts for a continuous process. The catalysts are preferably present in quantities of 0.1 to 3% by weight, based on the quantity of primary fatty alcohols in the reaction mixture. In a preferred embodiment, catalysts may also be used in quantities of 0.2 to 2% by weight, and more particularly, in quantities of 0.5 to 1.0% by weight. For a suspension process, a catalyst concentration of 0.1 to 2% by weight, based on the quantity of fatty alcohol used, has proved to be suitable, the preferred range being from 0.5 to 1.0% by weight Ni.

The reaction temperature required for the process is in the range from 180° C. to 300° C., preferably in the range from 200 to 280° C. and more particularly in the range from 220° to 260° C.

The reaction pressure suitable for the process is in the range from 2 to 300 bar, preferably in the range from 2 to 250 bar and more particularly in the range from 5 to 100 bar. The range from 5 to 80 bar is particularly preferred and the range from 10 to 50 bar most particularly preferred.

Water of reaction formed during the reaction has to be removed. Accordingly, it has proved to be of advantage to add hydrogen to the alcohol initially introduced with suspended catalyst and, at the same time, to remove water of reaction formed or reaction gases from the reactor. In a continuous process, the removal of water can take place, for example, in a multistage process. The reaction mixture formed then has to be filtered to remove catalyst. A fractional distillation is then carried out to remove the residual alcohol and traces of dimeric reaction products. The bottom product obtained can be recycled for the next reaction. A deodorization step may then be added on for odor improvement.

The present invention also relates to the use of the hydrocarbons produced by the above-described process in cosmetic preparations.

More particularly, odd-numbered hydrocarbons are readily obtainable by the process according to the invention. Accordingly, the present invention relates in particular to the use of linear, saturated odd-numbered alkanes containing 7 to 23 carbon atoms in cosmetic preparations. Examples of such alkanes include n-nonane, n-undecane, n-tridecane and n-heptadecane.

The present invention encompasses the use of individual hydrocarbons and mixtures of various hydrocarbons produced by the process according to the invention.

The hydrocarbons produced in accordance with the invention may be used for the production of cosmetic preparations such as, for example, hair shampoos, hair lotions, foam baths, shower baths, creams, gels, lotions, alcoholic and aqueous/alcoholic solutions, emulsions, wax/fat compounds, stick preparations, powders and ointments. These preparations may contain as further auxiliaries and additives mild surfactants, oil components, emulsifiers, pearlizing waxes, consistency factors, thickeners, superfatting agents, stabilizers, polymers, silicone compounds, fats, waxes, lecithins, phospholipids, biogenic agents, UV protection factors, antioxidants, deodorants, antiperspirants, antidandruff agents, film formers, swelling agents, insect repellents, self-tanning agents, tyrosine inhibitors (depigmenting agents), hydrotropes, solubilizers, preservatives, perfume oils, dyes and the like. The hydrocarbons are preferably used as oil components.

By virtue of the present invention, it is specifically possible to use hydrocarbons with a particular chain length as individual components in cosmetic formulations as so-called light emollients or even to mix them in a particular manner in order to be able to establish special properties such as, for example, spreading behavior, volatility or even flash points. More particularly, the possibility of mixing the hydrocarbons on the building block principle affords major advantages over hydrocarbons from petrochemical sources which are almost exclusively present as complex mixtures of branched and unbranched hydrocarbons. In cases such as these, further working up by distillation is only possible with considerable effort or would be attended by the problem of residues of unwanted isomers remaining in the product. In addition, the toxicological evaluation of a defined hydrocarbon or a defined hydrocarbon mixture, which is particularly important for cosmetic applications, is very much simpler and safer.

EXAMPLES

1) Production of tridecane from 1-tetradecanol 1000 grams of 1-tetradecanol (4.7 mol; Lorol C 14 from Cognis) were introduced into a stirrable pressure vessel with 10 grams of a nickel catalyst (Ni-5249 P from Engelhard; Ni content=63% by weight) and heated to 240° C. Hydrogen was then added over a period of 12 hours under a pressure of 20 bar through a gas dispersion tube and, at the same time, the reaction gases were removed through a valve in the lid of the reactor. The product was then cooled, drained off and filtered. A yield of 845 grams of reaction product was obtained.

GC analysis revealed the following composition: 89.0% tridecane, 2.1% tetradecane, 4.1% 1-tetradecanol, 4.2% dimeric reaction products.

The reaction product was then fractionated by distillation to pure tridecane and deodorized with nitrogen. A colorless, thinly liquid and substantially odorless product was obtained.

2) Production of undecane from 1-dodecanol 1000 grams of 1-dodecanol (5.4 mol; Lorol C 12 from Cognis) were introduced into a stirrable pressure vessel with 10 grams of a nickel catalyst (Ni-5249 P from Engelhard; Ni content=63% by weight) and heated to 240° C. Hydrogen was then added over a period of 8 hours under a pressure of 20 bar through a gas dispersion tube and, at the same time, the reaction gases were removed through a valve in the lid of the reactor. The product was then cooled, drained off and filtered. A yield of 835 grams of reaction product was obtained.

GC analysis revealed the following composition: 68.4% undecane, 0.6% dodecane, 21.7% 1-dodecanol, 7.2% dimeric reaction products.

The reaction product was then distilled to obtain pure undecane which was then deodorized with nitrogen. A colorless, thinly liquid and substantially odorless product was obtained.

3) Cosmetic Preparations Containing Undecane and Tridecane

The following Examples contain either undecane (obtained in accordance with Example 2) or tridecane (obtained in accordance with Example 1).

Example 3.1: All-Purpose Cream

| Phase | Component Trade name | INCI | % by wt. |
|---|---|---|---|
| I. | DEHYMULS ® E | Dicocoyl Pentaeryrithrityl Distearyl Citrate (and) Sorbitan Sesquioleate (and) Cera Alba (Beeswax) (and) Aluminium Stearates | 3.00 |
|  | DEHYMULS ® PGPH | Polyglyceryl 2 Dipolyhydroxystearate | 2.00 |
|  | CETIOL ® OE | Dicaprylyl Ether | 3.00 |
|  | CETIOL ® 868 | Ethylhexyl Stearate | 4.00 |
|  | MYRITOL ® 331 | Cocoglycerides | 2.00 |
|  | Undecane/Tridecane |  | 6.00 |
| II. | Glycerin, 86% |  | 5.00 |
|  | MgSO₄ × 7H₂O |  | 1.00 |
|  | Water, deionized |  | 74.00 |
| III. | Preservative |  | q.s. |

Production:

The components of phase I were melted at 80 to 85° C. and stirred to homogeneity. The components of phase II were heated to 80 to 85° C. and slowly added with stirring to phase I, followed by stirring for another 5 minutes at that temperature. The emulsion was then cooled with stirring and homogenized at 65 to 55° C. When the emulsion appeared homogeneous, it was further cooled to 30° C. with stirring. The components of phase III were then added, followed by further stirring.

Example 3.2: Balm for Moistening and Protecting the Lips

| Phase | Component Trade name | INCI | % by wt. |
|---|---|---|---|
| I. | Cerilla Raffinée G* | Candelilla (*Euphorbia Cerifera*) Wax | 7.53 |
|  | CUTINA ® LM conc. | Polyglyceryl-2 Dipolyhydroxystearate and Octyldodecanol and *Copemicia Cerifera* (Carnauba) Wax and *Euphorbia Cerifera* (Candelilla) Wax and Beeswax and Cetearyl Glucoside and Cetearyl Alcohol | 6.57 |
|  | Paracera M (Paramelt) | Mycrocrystalline Wax | 2.45 |
|  | Cerewax M85/C(SCLR) | Ceresin | 2.08 |
|  | Colophane claire type Y | Rosin | 1.89 |
|  | Cerauba T1* | Carnauba (*Copernica Cerifera*) Wax | 1.86 |
|  | Cerabeil blanche 1* | Beeswax | 0.78 |
|  | Undecane/Tridecane |  | 15.57 |
|  | EUTANOL ® G | Octyldodecanol | 14.87 |
|  | Vaseline F7850(Fina) | Petrolatum | 6.84 |
|  | Crodamol ML(Croda) | Myristyl Lactate | 1.13 |
|  | ELESTAB ®366 |  | 0.43 |
| II. | Castor oil | Castor Oil | 35.00 |
| III. | IRWINOL ® LS 9319 | African wild mango butter | 3.00 |

*obtainable from Lambert-Rivière (France)

Production:

Phase I was melted at 85° C., phase II was added and the temperature was kept at 80° C. Phase III was added shortly before pouring into the mold (moistened with Dimethicone 50 cts and preheated to 40° C.). The melt was poured into the mold and cooled to 40° C. The mold was cooled to around 0° C. in a refrigerator.

Example 3.3: Styling Wax

| Phase | Component Trade name | INCI | % by wt. |
|---|---|---|---|
| I. | CUTINA ® MD | Glyceryl Stearate | 14.50 |
|  | COMPERLAN ® 100 | Cocamide MEA | 2.50 |
|  | CUTINA ® HR Powder | Hydrogenated Castor Oil | 2.50 |
|  | PLANTACARE ® 1200 UP | Lauryl Glucoside | 5.00 |
|  | LANETTE ® O | Cetearyl Alcohol | 7.00 |
|  | CUTINA ® CP | Cetyl Palmitate | 7.00 |
|  | EUMULGIN ® O 20 | Ceteleth-20 | 5.00 |
|  | Undecane/Tridecane |  | 23.50 |
|  | Vaseline | Petrolatum | 32.50 |
|  | Wacker Siliconoil AK 350 | Dimethicone | 0.50 |

The styling wax was produced by heating all the components to 80° C. and homogenization.

Example 3.4: Moisturizing Body Milk

| Phase | Component Trade name | INCI | % by wt. |
|---|---|---|---|
| I. | EMULGADE ® CM | Cetearyl Isononanoate (and) Ceteareth-20 (and) Cetearyl Alcohol (and) Glyceryl Stearate (and) Glycerin (and) Ceteareth | 5.0 |
|  | EUMULGIN ® VL 75 | Lauryl Glucoside (and) Polyglyceryl-2 Dipolyhydroxystearate (and) Glycerin | 2.0 |
|  | CETIOL ® OE | Dicaprylyl Ether | 4.0 |
|  | CETIOL ® J 600 | Oleyl Erucate | 1.0 |

| Phase | Component Trade name | INCI | % by wt. |
|---|---|---|---|
| | ISOPROPYL-MYRISTATE | Isopropyl Myristate | 7.0 |
| | Undecane/Tridecane | | 7.0 |
| II. | Water, deionized | | to 100 |
| III. | Sepigel 305 (Seppic) | Polyacrylamide | 1.0 |
| IV. | HISPAGEL ® 200 | Glycerin (and) Glyceryl Polyacrylate | 20.0 |
| V. | Preservative, perfume | | q.s. |
| | pH | | 5.5 |

The moisturizing body milk was produced by mixing phase I and water with stirring at room temperature. Phase III was then added and stirring was continued until a homogeneous, swollen mixture was obtained. Phase IV was then added, followed by phase 5. The pH was then adjusted.

Example 3.5: o/w Soft Cream

| Phase | Component Trade name | INCI | % by wt. |
|---|---|---|---|
| I. | EMULGADE ® SE-PF | Glyceryl Stearate (and) Ceteareth-20 (and) Ceteareth-12 (and) Stearyl Alcohol (and) Ceteareth-20 (and) Distearyl Ether | 6.0 |
| | LANETTE ® O | Cetearyl Alcohol | 1.0 |
| | CUTINA ® MD | Glyceryl Stearate | 2.0 |
| | CETIOL ® MM | Myristyl Myristate | 2.0 |
| | Undecane/Tridecane | | 8.0 |
| | Jojoba Oil | *Simmondsia Chinensis* (jojoba) Seed Oil | 2.0 |
| | COPHEROL ® 1250 | Tocopheryl Acetate | 0.5 |
| | | Dimethicone | 0.5 |
| | | Cyclomethicone | 3.0 |
| II. | Water | Aqua | to 100 |
| | | Propylene Glycol | 3.0 |
| III. | HISPAGEL ® 200 | Glycerin (and) Glyceryl Polyacrylate | 15.0 |
| IV. | Preservative | | q.s. |
| | pH | | 5.5-6.5 |

The cream was produced by heating phase I to 80° C. Phase II was also heated to 80° C. and added to phase I with stirring. The resulting mixture was cooled with stirring and homogenized at about 55° C. with a suitable dispersing device (for example Ultra Turrax). Phase III was then introduced with continuous stirring, phase IV was added and the pH was adjusted.

Example 3.6: o/w Cream

| Phase | Component Trade name | INCI | % by wt. |
|---|---|---|---|
| I. | MONOMULS ® 90 O 18 | Glyceryl Oleate | 2.00 |
| | LAMEFORM ® TGI | Polyglyceryl 3 Diisostearate | 4.00 |
| | CETIOL ® A | Hexyl Laurate | 12.00 |
| | Undecane/Tridecane | | 9.00 |
| | SIPOL ® C 16/18 OR | Cetearyl Alcohol | 1.00 |
| | Beeswax | Beeswax | 3.00 |
| | Zinc stearate | Zinc Stearate | 2.00 |
| | Zinc Oxide | Cl 77947 (or) Zinc Oxide | 15.00 |
| | Magnesium Sulfate | Magnesium Sulphate | 1.00 |
| | Glycerin | Glycerin | 3.00 |
| | Preservative | | q.s. |
| | Benzyl Alcohol | Benzyl Alcohol | 0.40 |
| | HYDAGEN ® B | Bisabolol | 0.50 |
| | Irgasan DP300 | Triclosan | 0.05 |
| | Water | Aqua | 100.00 |

The first 8 components were melted at 85° C. The magnesium sulfate and glycerin were dissolved in the water and the resulting mixture was heated to 85° C. This aqueous phase was added to the oil phase and the combined phases were dispersed. The dispersion was cooled to 40° C. with continuous stirring, after which the benzyl alcohol, Hydagen B and Irgasan DP300 were mixed and added to the emulsion. The whole was cooled to 30° C. with continued stirring and homogenized.

Example 3.7: Body Wash Cleansing Emulsion

| Phase | Component Trade name | INCI | % by wt. |
|---|---|---|---|
| I. | Texapon ALS-IS | Ammonium Lauryl Sulfate | 30.00 |
| | TEXAPON ® NSO | Sodium Laureth Sulfate | 18.00 |
| | Undecane/Tridecane | | 18.00 |
| | Plantacare ® 1200 | Lauryl Glucoside | 8.00 |
| II. | Jaguar HP 105 | Hydroxypopyl Guar | 2.00 |
| | Euxyl K400 | Methyldibromo Glutaronitrile and Phenoxyethanol | 0.10 |
| | Water | Aqua | 23.90 |
| | pH-value | | 5.6 |

TABLE 1

O/W sun protection emulsions
The following Examples all contain either undecane (obtained in accordance with Example 2) or tridecane (obtained in accordance with Example 1). All quantities are in % by weight.

| | Component | | | | | | | | | | |
|---|---|---|---|---|---|---|---|---|---|---|---|
| L = Lotion, C = Cream | 1 L | 2 C | 3 S | 4 L | 5 C | 6 L | 7 L | 8 C | 9 L | 10 C | 11 L |
| Eumulgin ® VL 75 | | | | | | 4 | 4 | 2 | | | |
| Eumulgin ® B2 | | 2 | | | | | | | | | |
| Tween ® 60 | | | | | 1 | | | | | | |
| Myrj ® 51 | | | 3 | | 2 | | | | | | |
| Cutina ® E 24 | 1 | | | | 1 | | | | | | |
| Hostaphat ® KL 340 N | | | | | | | | | | 2 | |
| Lanette ® E | | | | 0.5 | | | | | | 0.5 | |

TABLE 1-continued

O/W sun protection emulsions
The following Examples all contain either undecane (obtained in accordance with Example 2) or tridecane (obtained in accordance with Example 1). All quantities are in % by weight.

| L = Lotion, C = Cream | 1 L | 2 C | 3 S | 4 L | 5 C | 6 L | 7 L | 8 C | 9 L | 10 C | 11 L |
|---|---|---|---|---|---|---|---|---|---|---|---|
| Amphisol ® K | | | 1 | | | 1 | | 0.5 | | 1 | |
| Sodium stearate | | | | | | | 1 | | | | 2 |
| Emulgade ® PL 68/50 | | | 1 | | 5 | | | | | 4 | |
| Tego ® Care 450 | | | | | | | | | | 3 | |
| Cutina ® MD | 2 | | | 6 | | | 4 | | | 6 | |
| Lanette ® 14 | 1 | | | 1 | | | | 2 | | | 4 |
| Lanette ® O | 1 | 6 | | | 5 | 2 | | 2 | | | |
| Antaron V 216 | | | 1 | | 2 | 2 | | | | 1 | |
| Emery ® 1780 | | | | | 0.5 | 0.5 | | | | | |
| Lanolin, anhydrous, USP | | | | | | | | 5 | | | |
| Undecane or tridecane | 2 | 2 | 4 | 1 | 2 | 2 | 2 | 1 | 2 | 2 | 1 |
| Myritol ® PC | | | | | 5 | | | | | | |
| Myritol ® 331 | 5 | | 8 | | | 6 | | 10 | | 2 | |
| Finsolv ® TN | | | 1 | | | | | 1 | 8 | | |
| Cetiol ® CC | | 2 | 5 | | | 4 | 4 | 2 | | 2 | |
| Cetiol ® OE | | | 3 | | | | | | 2 | 3 | |
| Dow Corning DC ® 244 | 4 | | 1 | | 5 | | | 2 | | | 2 |
| Dow Corning DC ® 2502 | | 1 | | | 2 | | | | | | |
| Squatol ® S | | | | | | | 4 | | | | |
| Silikonöl Wacker AK ® 350 | | 2 | | | | | | | | | |
| Cetiol ® 868 | | | | | | 2 | | 4 | | | 7 |
| Cetiol ® J 600 | | | | | | 3 | 2 | | | 5 | |
| Mineral oil | | | | | 9 | | | | | | |
| Cetiol ® B | | | 1 | | | | | | | 2 | |
| Eutanol ® G | | | | | | | | | | | |
| Eutanol ® G 16 | | | | | | | | | | | |
| Cetiol ® PGL | | | 5 | | | | | | | 5 | |
| Almond oil | | | 2 | | | | 1 | | | | |
| Photonyl ® LS | | | | 2 | | | | | | 2 | |
| Panthenol | | | | | | | 1 | | | | |
| Bisabolol | | | | | | | 0.2 | | | | |
| Tocopherol/Tocopherylacetate | | | | | | | 1 | | | | |
| Photonyl ® LS | | | | | | | | | | | |
| Neo Heliopan ® Hydro (Na salt) | 2 | | 2.2 | | 3 | 3 | | | | | 2 |
| Neo Heliopan AP (Na salt) | 2 | | | | 1.5 | 2 | 2 | | 1 | | 1 |
| Neo Heliopan ® 303 | 3 | 5 | 9 | 4 | | | | | | | |
| Neo Heliopan ® BB | | | | | 1 | | | | | | 2 |
| Neo Heliopan ® MBC | 2 | | | 3 | | 2 | 2 | 2 | | | 1 |
| Neo Heliopan ® OS | | | | | | | | | 10 | 7 | |
| Neo Heliopan ® E 1000 | | 7.5 | | 6 | | | 7.5 | 4 | | | 6 |
| Neo Heliopan ® AV | | | 7.5 | | | | 7.5 | 4 | 5 | | |
| Uvinul ® T 150 | 2 | | | | 2.5 | | | 1 | | | |
| Parsol ® 1789 | | 1 | 1 | | | | 2 | | 2 | 2 | |
| Zinc oxide NDM | 10 | | 5 | | | 10 | | 3 | | 5 | 4 |
| Eusolex ® T 2000 | | | | | 5 | | 3 | 3 | | | 4 |
| Veegum ® Ultra | | | 0.75 | | | | | 1 | 1 | | |
| Keltrol ® T | | | 0.25 | | | | | 0.5 | 0.5 | | |
| Carbopol ® 980 | | 0.5 | | 0.2 | 0.2 | 0.2 | | 0.5 | 0.1 | 0.3 | 0.2 |
| Ethanol | | | | | | | | | | 10 | |
| Butyleneglycol | | 2 | | 4 | 3 | | 2 | 5 | 2 | | 2 |
| Glycerin | 5 | 5 | 5 | | 3 | 3 | 2 | | 4 | | 3 |
| Preservative, NaOH | | | | | | q.s. | | | | | |
| Water | | | | | | to 100 | | | | | |

TABLE 2

O/W sun protection emulsions

| L = Lotion, C = Cream | 12 L | 13 L | 14 L | 15 C | 16 L | 17 C | 18 S | 19 C | 20 C | 21 L | 22 L |
|---|---|---|---|---|---|---|---|---|---|---|---|
| Eumulgin ® VL 75 | 4 | 3 | 4.5 | | 3 | | | | 4 | | |
| Eumulgin ® B2 | | | | | | | | | | 1 | |
| Tween ® 60 | | | | | | | | | | | 1 |
| Myrj ® 51 | | | | | | | | | | | |
| Cutina ® E 24 | | | | 2 | | | | | | | |

TABLE 2-continued

O/W sun protection emulsions

| L = Lotion, C = Cream | 12 L | 13 L | 14 L | 15 C | 16 L | 17 C | 18 S | 19 C | 20 C | 21 L | 22 L |
|---|---|---|---|---|---|---|---|---|---|---|---|
| Hostaphat ® KL 340 N | | | | | | | | | 0.5 | | |
| Lanette ® E | 0.5 | | 0.5 | 0.5 | | | 0.1 | | 0.5 | | |
| Amphisol ® K | 0.5 | | | | | 1 | 1 | 1 | | | |
| Sodium stearate | | | | | 1 | | | | | | |
| Emulgade ® PL 68/50 | | 6 | | | | 4.5 | 1 | | 5 | | |
| Tego ® Care 450 | 1 | | | | | | | | 4 | | |
| Cutina ® MD | 1 | | | 8 | 6 | 1 | | | | 4 | 1 |
| Lanette ® 14 | | 2 | | | | | | 2 | | 1 | |
| Lanette ® O | | | | 2 | | | | | 1 | 1 | |
| Antaron V 220 | 1 | | | 2 | | | 0.5 | | | 2 | 0.5 |
| Undecane or tridecane | 4 | 2 | 4 | 6 | 10 | 4 | 2 | 8 | 2 | 1 | 3 |
| Myritol ® PC | | | | | | | | | 5 | | |
| Myritol ® 331 | 12 | | 12 | | | 8 | 8 | | | 10 | 8 |
| Finsolv ® TN | | | | | 5 | | | 3 | 3 | | |
| Cetiol ® CC | 6 | | 6 | | | 5 | 5 | | | | |
| Cetiol ® OE | | | | | 2 | | | | | | 2 |
| Dow Corning DC ® 244 | | 2 | | | 1 | | | | | | |
| Dow Corning DC ® 2502 | | 1 | | | 1 | | | | | | |
| Ceraphyl ® 45 | | | | | | | | | | 2 | 2 |
| Silikonöl Wacker AK ® 350 | | | | | 1 | | | | | | |
| Cetiol ® 868 | | 2 | | | | | | | | | |
| Cetiol ® J 600 | | 2 | | | | | | | | | |
| Mineral oil | | | | 10 | | | | | | | |
| Cetiol ® B | 4 | | 4 | | | | | 4 | | | |
| Eutanol ® G | | 3 | | | | 3 | | | | | |
| Eutanol ® G 16 S | 10 | | | | | | | | | | |
| Cetiol ® PGL | | | | | | | | | 2 | | |
| Photonyl ® LS | | | | | | | | | | 2 | |
| Panthenol | | | | | | 1 | | | | | |
| Bisabolol | | | | | | 0.2 | | | | | |
| Tocopherol/Tocopherylacetate | | | | | | 1 | | | | | |
| Neo Heliopan ® Hydro (Na salt) | | | | | | | | | | 3 | |
| Neo Heliopan AP (Na salt) | | 2 | | 2 | | | 2 | | | | 1 |
| Eusolex ® OCR | 6 | | 9 | | 5 | 7 | 9 | | 4 | | 7 |
| Neo Heliopan ® BB | | | | | | | | 1 | 1 | | 1 |
| Neo Heliopan ® MBC | | 2 | | 1 | | | | 3 | 1 | | 3 |
| Neo Heliopan ® OS | 2 | | | | | | | | 7 | | |
| Neo Heliopan ® E1000 | | 4 | | | | | | 5 | | | |
| Neo Heliopan ® AV | | 4 | 7.5 | 5 | | | | 5 | 4 | 7.5 | |
| Uvinul ® T 150 | 1 | | | | | | | | 1.3 | 1 | 1 |
| Parsol ® 1789 | 1 | | | | | | | | 2 | | 1 |
| Z-Cote ® HP 1 | 7 | 2 | 5 | | | 7 | 5 | | 6 | 2 | |
| Eusolex ® T 2000 | 5 | 2 | | | 10 | | 10 | | | 2 | |
| Veegum ® Ultra | 1.5 | | 1.5 | | | 1.5 | 1.2 | | 1 | | |
| Keltrol ® T | 0.5 | | 0.5 | | | 0.5 | 0.4 | | 0.5 | | |
| Pemulen ® TR 2 | | 0.3 | | 0.3 | | | 0.1 | 0.2 | | | 0.3 |
| Ethanol | | 5 | | 8 | | | | | | | |
| Butyleneglycol | 1 | | | 3 | 3 | | | | | 8 | 1 |
| Glycerin | 2 | 4 | 3 | 3 | | 3 | 3 | 3 | 5 | | 3 |
| Water/preservative/NaOH | | | | | to 100/q.s./q.s | | | | | | |

TABLE 3

W/O sun protection emulsions
E

| L = Lotion; C = Cream | 23 C | 24 L | 25 C | 26 L | 27 C | 28 L | 29 L | 30 L | 31 L | 32 C | 33 C |
|---|---|---|---|---|---|---|---|---|---|---|---|
| Dehymuls ® PGPH | 4 | 2 | 1 | 3 | 3 | 1 | 1 | 2 | 2 | 4 | 1 |
| Monomuls ® 90-O18 | | | 2 | | | | | | | | |
| Lameform ® TGI | 2 | | 4 | | 3 | | | | | 1 | 3 |
| Abil ® EM 90 | | | | | | | 4 | | | | |
| Glucate ® DO | | | | | | | | | | | 3 |
| Isolan ® PDI | | | | | | 4 | | 2 | | | |
| Arlacel ® 83 | | | | 2 | | | | | | | |
| Elfacos ® ST9 | | | | | | | | | | 2 | |
| Elfacos ® ST37 | | | | | | | | | | | |

TABLE 3-continued

W/O sun protection emulsions
E

| L = Lotion; C = Cream | 23 C | 24 L | 25 C | 26 L | 27 C | 28 L | 29 L | 30 L | 31 L | 32 C | 33 C |
|---|---|---|---|---|---|---|---|---|---|---|---|
| Arlacel ® P 135 | | 2 | | | | | | | | | |
| Dehymuls ® HRE 7 | | | | | | | | | | | |
| Zinc stearate | 1 | | | 1 | 1 | | | 1 | | 1 | |
| Microcrystalline wax | | | 5 | | | 2 | | | | | 5 |
| Beeswax | 1 | | | 1 | | | | 5 | | 7 | |
| Tego ® Care CG | | | | | 1 | | | | | | 5 |
| Prisorine ® 3505 | 1 | | 1 | 1 | | 1 | 1 | | | | 1 |
| Emery ® 1780 | | | 5 | | | | | | | 4 | |
| Wool wax alcohol, anhydrous, USP | | | | | | | | | | | 1 |
| Antaron V 216 | 2 | | | | | | | | | | |
| Undecane or tridecane | 3 | 4 | 2 | 1 | 10 | 2 | 2 | 6 | 3 | 12 | 1 |
| Myritol ® PC | | | | | 3 | | | 4 | | | |
| Myritol ® 331 | 10 | | | | 3 | 6 | | | | | 8 |
| Finsolv ® TN | | | | 5 | | | 5 | | | | |
| Cetiol ® CC | 12 | 22 | | | | 2 | | | 2 | | 5 |
| Cetiol ® OE | | | | | 4 | | 5 | | 4 | 2 | |
| Dow Corning DC ® 244 | | | | | | | 2 | | | | |
| Dow Corning DC ® 2502 | | | 1 | | 2 | | | | | | |
| Prisorine ® 3758 | | | | | | | | | | 2 | |
| Silikonöl Wacker AK ® 350 | | | | 4 | | | | 3 | | | |
| Cetiol ® 868 | | | | | | | | | | 2 | |
| Eutanol ® G 16 | | 3 | | | | | | | | | |
| Eutanol ® G 16S | | | | | | | | | | | |
| Cetiol ® J 600 | | | 4 | | | 2 | | | | | |
| Ceraphyl ® 45 | | | | 2 | | | | 2 | | 6 | |
| Mineral oil | | | | | 4 | | | | | | |
| Cetiol ® B | | | 2 | 4 | | | | | | 3 | |
| Eutanol ® G | | | 3 | | | | | 8 | | | |
| Cetiol ® PGL | | 11 | | | | 4 | | | 9 | | |
| Almond oil | | | | | 1 | | 5 | | | | |
| Photonyl ® LS | | | 2 | 1 | | | | | 4 | | |
| Panthenol | | | | | | 1.0 | | | | | |
| Bisabolol | | | | | | 0.2 | | | | | |
| Tocopherol/Tocopherylacetate | | | | | | 1.0 | | | | | |
| Magnesium sulfate × 7 water | 1 | | | | | | | | | | |
| Neo Heliopan ® Hydro (Na salt) | | 2 | | 3 | | | | 2 | | | |
| Neo Heliopan AP (Na salt) | 2 | 1 | | | 2 | | | 1 | 2 | | 1 |
| Neo Heliopan ® 303 | | | | | 4 | | | | | 6 | |
| Neo Heliopan ® BB | | 4 | 2 | | | | 2 | | | | |
| Neo Heliopan ® MBC | | | | | | | | 4 | | 3 | |
| Neo Heliopan ® OS | | | | | | | | | | | |
| Neo Heliopan ® E 1000 | | | | | | | | | 5 | | |
| Neo Heliopan ® AV | | 3 | 6 | 6 | | 7.5 | 7.5 | | 5 | | 7.5 |
| Uvinul ® T 150 | | | | | 2.5 | | | 1 | | 2 | |
| Parsol ® 1789 | | 2 | | | | | | 1 | | 2 | |
| Zinc oxide NDM | | | | | | 6 | | | | | |
| Eusolex ® T 2000 | 15 | | 10 | | 5 | | 4 | | | 4 | |
| Ethanol | | | | | | | | | 8 | | |
| Butyleneglycol | | | 2 | 6 | | | 2 | 5 | | | 2 |
| Glycerin | 5 | 3 | 3 | | 5 | 3 | 2 | | 10 | 4 | |
| Water, preservative | | | | | to 100, q.s. | | | | | | |

TABLE 4

W/O sun protection emulsions

| L =Lotion; C = Cream | 34 L | 35 C | 36 L | 37 L | 38 C | 39 L | 40 L | 41 L | 42 L | 43 C | 44 C |
|---|---|---|---|---|---|---|---|---|---|---|---|
| Dehymuls ® PGPH | 3 | 1 | 5 | 1 | 1 | 3 | 2 | 4 | 0.5 | 1 | 4 |
| Monomuls ® 90-O18 | | 1 | | | | | | | | | |
| Lameform ® TGI | | | | | 4 | | | 1 | | 3 | 1 |
| Abil ® EM 90 | | | | 1 | | | | | 2 | | |
| Glucate ® DO | | | | 3 | | | | | 2 | | |
| Isolan ® PDI | | | 3 | | | | 4 | | | | |
| Arlacel ® 83 | | | | | | 3 | | | | | |
| Elfacos ® ST9 | | | | | | | | | | | 2 |

TABLE 4-continued

W/O sun protection emulsions

| L =Lotion; C = Cream | 34 L | 35 C | 36 L | 37 L | 38 C | 39 L | 40 L | 41 L | 42 L | 43 C | 44 C |
|---|---|---|---|---|---|---|---|---|---|---|---|
| Elfacos ® ST37 | 2 | | | | | | | | | | |
| Arlacel ® P 135 | | | | | | 3 | | | | | |
| Dehymuls ® HRE 7 | | | | | | | | | 4 | | |
| Zinc stearate | | 2 | 2 | 1 | 1 | | | 1 | 1 | | |
| Microcrystalline wax | | | | | 4 | | 1 | | | 4 | |
| Beeswax | | 4 | | 2 | | | 1 | | 2 | | 1 |
| Tego ® Care CG | | | | | | | | | | | |
| Isostearic acid | 1 | 1 | | | | | 1 | 1 | | 1 | 1 |
| Emery ® 1780 | | 7 | 3 | | | | | | | | |
| Wool wax alcohol, anhydrous, USP | | | | | | | | | | | |
| Antaron V 220 | | 0.5 | 2 | 1 | 1 | 1 | | | | | |
| Undecane or tridecane | 2 | 4 | 3 | 3 | 2 | 2 | 1 | 3 | 3 | 1 | 4 |
| Myritol ® PC | | | | | | | | | | | |
| Myritol ® 331 | 4 | 2 | 3 | | 5 | | | 8 | 5 | 4 | |
| Finsolv ® TN | | 5 | 5 | | | 7 | | | | | |
| Cetiol ® CC | 3 | 1 | | | | | 3 | 16 | | | 12 |
| Cetiol ® OE | | 3 | | 2 | | | 3 | | | | |
| Dow Corning DC ® 244 | | 4 | | 2 | | | | | | | |
| Dow Corning DC ® 2502 | | | | 1 | | | | | | | |
| Prisorine ® 3578 | | 1 | | | | | | | | | |
| Silikonöl Wacker AK ® 350 | | | | 1 | | | | | | | |
| Cetiol ® 868 | | | | | | | | | | | |
| Eutanol ® G 16 | | | | | | | | | | | 3 |
| Eutanol ® G 16S | | | | | | | | | | | 7 |
| Cetiol ® J 600 | | | | 3 | | | | | | | |
| Ceraphyl ® 45 | | | | 1 | | | | | 5 | 4 | |
| Mineral oil | | | | | | | 9 | | | | |
| Cetiol ® B | | | | | 3 | 3 | | | 2 | 2 | |
| Eutanol ® G | | | | 2 | | | | | 5 | | |
| Cetiol ® PGL | | | | | | | | 2 | | | |
| Almond oil | | | 2 | | | | | | | | |
| Photonyl ® LS | | | | | | | 3 | | | | 2 |
| Panthenol | | | | | | 1.0 | | | | | |
| Bisabolol | | | | | | 0.2 | | | | | |
| Tocopherol/Tocopherylacetate | | | | | | 1.0 | | | | | |
| Magnesium sulfate x 7 water | | | | | | 1 | | | | | |
| Neo Heliopan ® Hydro (Na salt) | | 4 | | | | | 4 | | | | |
| Neo Heliopan AP (Na salt) | 2 | | | 1 | 2 | | 1 | | | | |
| Neo Heliopan ® 303 | 6 | 2 | | | | | | | 6 | | |
| Neo Heliopan ® BB | | 2 | | 2 | | 2 | | | | | |
| Neo Heliopan ® MBC | 2 | | | | 3 | | 4 | | 2 | | |
| Neo Heliopan ® OS | | | | | 10 | | 8 | | | | |
| Neo Heliopan ® E 1000 | | | | 5 | 6 | | | | | 5 | |
| Neo Heliopan ® AV | | 5 | 5 | | | 7.5 | | | | 5 | |
| Uvinul ® T 150 | 1 | | | | 2 | 2 | | | | 3 | 2 |
| Parsol ® 1789 | | 1 | 1 | | | | 1 | | | 0.5 | |
| Z-Cote ® HP 1 | 4 | 10 | | | | | | 5 | | | 5 |
| Titanium dioxide T 805 | | | | | 2 | 3 | | 7 | | 4 | 7 |
| Ethanol | | | | | 8 | 10 | | | | | |
| Butyleneglycol | 5 | 1 | | 3 | 3 | | | | 8 | 2 | |
| Glycerin | | | 6 | 2 | | | 5 | 5 | | 3 | 5 |
| Water, preservative | to 100, q.s. | | | | | | | | | | |

TABLE 5

W/O care emulsions

| L = Lotion, C = Cream | 45 C | 46 L | 47 C | 48 L | 49 C | 50 L | 51 L | 52 L | 53 C | 54 C | 55 C |
|---|---|---|---|---|---|---|---|---|---|---|---|
| Dehymuls ® PGPH | 1 | 3 | 1 | 2 | 3 | 1 | 1 | 2 | 1 | 1 | 1 |
| Monomuls ® 90-O18 | 2 | | | | | | | | 2 | | 2 |
| Lameform ® TGI | 4 | 1 | | | 3 | | | 1 | 4 | 3 | 3 |
| Abil ® EM 90 | | | | | | 4 | | | | | |
| Isolan ® PDI | | | | | 4 | | | | | | |
| Glucate ® DO | | | | 5 | | | | | | | |
| Arlacel ® 83 | | | 5 | | | | | | | | |
| Dehymuls ® FCE | | | | | | | | | | | |

TABLE 5-continued

W/O care emulsions

| L = Lotion, C = Cream | 45 C | 46 L | 47 C | 48 L | 49 C | 50 L | 51 L | 52 L | 53 C | 54 C | 55 C |
|---|---|---|---|---|---|---|---|---|---|---|---|
| Dehymuls ® HRE 7 | | | | | | | | 4 | | 1 | |
| Zinc stearate | 2 | 1 | | 1 | 1 | | | 1 | 1 | 1 | |
| Microcrystalline wax | | | 5 | | | 2 | | | | | 5 |
| Beeswax | 4 | | | 1 | | | | 1 | 4 | 7 | |
| Tego Care ® CG | | | | | 1 | | | | | | 0.5 |
| Prisorine ® 3505 | | | 1 | 1 | | 1 | 1 | | | | 1 |
| Dry Flo ® Plus | | | | | | | | | | | |
| SFE 839 | | | | | | | 3 | | | | |
| Emery ® 1780 | 1 | | | | | | | | | | 1 |
| Lanolin; anhydrous USP | | | 5 | | | | | | | 4 | |
| Undecane or tridecane | 3 | 4 | 2 | 12 | 10 | 2 | 2 | 6 | 3 | 12 | 1 |
| Cegesoft ® C 17 | | | 3 | | | | | | | 1 | |
| Myritol ® PC | | | | | | 2 | | 4 | | | |
| Myritol ® 331 | | 6 | | | 2 | 6 | 2 | | | | 8 |
| Finsolv ® TN | | | | 5 | | 2 | 5 | | | | |
| Cetiol ® A | | 6 | | | 4 | | | | | | |
| Cetiol ® CC | | 8 | | | 2 | 2 | 2 | | | | 5 |
| Cetiol ® SN | | 5 | | | | | | | 3 | | |
| Cetiol ® OE | 3 | | | | 4 | | 2 | | 4 | 2 | |
| Dow Corning DC ® 244 | | | | | 1 | | 2 | | | | |
| Dow Corning DC ® 2502 | | | 1 | | 2 | | | | | | |
| Prisorine ® 3758 | | | | | 3 | | | | | | |
| Silikonöl Wacker AK ® 350 | | | | 4 | | | | | 3 | | |
| Cetiol ® 868 | | | | | | | | | | 2 | 7 |
| Cetiol ® J 600 | | | 4 | | | 2 | | | | | |
| Ceraphyl ® 45 | | | | 2 | | | | | 2 | 6 | |
| Mineral oil | | | | | 4 | | | | | | |
| Cetiol ® B | | | 2 | 4 | | | | | | 3 | |
| Eutanol ® G 16 | | 1 | | | | | | | | 3 | |
| Eutanol ® G | | | 3 | | | | | 8 | | | |
| Cetiol ® PGL | | | | | | | 4 | | | 9 | |
| Almond oil | | | | | 1 | | 5 | | | | |
| Insect Repellent ® 3535 | 2 | | | | | | | | | | |
| N,N-Diethyl-m-toluamide | | | | 3 | | | | | 5 | | |
| Photonyl ® LS | 2 | 2 | | | | | | | | | |
| Panthenol | | | | | | 1.0 | | | | | |
| Bisabolol | | | | | | 0.2 | | | | | |
| Tocopherol/Tocopheryl Acetate | | | | | | 1.0 | | | | | |
| Magnesium sulfate × 7 water | | | | | | 1 | | | | | |
| Bentone ® 38 | | | | | 1 | | | | | | |
| Propylenecarbonate | | | | | 0.5 | | | | | | |
| Ethanol | | | | | | | | | | 8 | |
| Butylene Glycol | | | 2 | 6 | | | 2 | 5 | | | 2 |
| Glycerin | 5 | 3 | 3 | | 5 | | 3 | 2 | 10 | 4 | |
| Water, preservative | | | | | to 100, q.s. | | | | | | |

TABLE 6

W/O care emulsions

| L = Lotion, C = Cream | 56 L | 57 C | 58 L | 59 L | 60 C | 61 L | 62 L | 63 L | 64 L | 65 C | 66 C |
|---|---|---|---|---|---|---|---|---|---|---|---|
| Dehymuls ® PGPH | 3 | 1 | 5 | 1 | 1 | 3 | 3 | 4 | 1 | 1 | 1 |
| Monomuls ® 90-O18 | | 1 | | 1 | | | | | | | |
| Lameform ® TGI | | | | | 4 | | | 1 | 3 | | |
| Abil ® EM 90 | | | | 3 | | | | | 2 | | |
| Isolan ® PDI | | 3 | | | | | | | | | 4 |
| Glucate ® DO | 1 | | | | | | | | | | |
| Arlacel ® 83 | | | | | 3 | | | | | | |
| Dehymuls ® FCE | | | | 4 | | 1 | | | | | |
| Dehymuls ® HRE 7 | | | | | | | | | 7 | | |
| Zinc stearate | | 2 | 2 | 1 | 1 | 1 | | 1 | 1 | | 1 |
| Microcrystalline wax | | | 1 | | 4 | | 1 | | | 4 | |
| Beeswax | | 4 | | 2 | | 2 | 1 | 1 | 2 | | 5 |
| Tego ® Care CG | | | | | | | | | | | |
| Prisorine ® 3505 | 1 | 1 | | | | 1 | 1 | | | 1 | 1 |
| Dry Flo ® Plus | 1 | | | | | | | | | | |

TABLE 6-continued

W/O care emulsions

| L = Lotion, C = Cream | 56 L | 57 C | 58 L | 59 L | 60 C | 61 L | 62 L | 63 L | 64 L | 65 C | 66 C |
|---|---|---|---|---|---|---|---|---|---|---|---|
| SFE ® 839 | | 5 | | | | 4 | | | | | |
| Emery ® 1780 | | | | | | | | | | | |
| Lanolin anhydrous USP | | 7 | 3 | | | | | | | | |
| Undecane or tridecane | 3 | 4 | 4 | 8 | 10 | 2 | 8 | 6 | 3 | 12 | 7 |
| Cegesoft ® C 17 | | 2 | | | | | | | | | |
| Myritol ® PC | | | | 8 | | | | | | | |
| Myritol ® 331 | 4 | | 3 | | 5 | 3 | | | 5 | 4 | |
| Finsolv ® TN | | | 5 | | | 7 | | | | | |
| Cetiol ® A | | | | | | | 6 | | | | |
| Cetiol ® CC | 3 | | | 6 | | 3 | 3 | | 8 | | |
| Cetiol ® SN | | | | | 5 | | | | | | |
| Cetiol ® OE | | | 3 | 2 | | | 3 | | | | 8 |
| Dow Corning ® DC 244 | | 4 | | 2 | | 2 | | | | | |
| Dow Corning ® DC 2502 | | | 1 | | | | | | | | |
| Prisorine ® 3758 | | | | | | 1 | | | | | |
| Silikonöl Wacker AK ® 350 | | | | 1 | | 1 | | 4 | | | |
| Cetiol ® 868 | | | | | | | | | | | 10 |
| Cetiol ® J 600 | 4 | | | 3 | | | | | | | |
| Ceraphyl ® 45 | | | | 1 | | | | | 5 | 4 | |
| Mineral oil | | | | | | | 9 | | | | |
| Cetiol ® B | | | | 3 | | 3 | | 2 | 2 | | |
| Eutanol ® G 16 | 1 | | | | | | | | | | |
| Eutanol ® G | | | | 2 | | | | | 5 | | |
| Cetiol ® PGL | | | 10 | | | | | 6 | | | 3 |
| Almond oil | | | 2 | | 5 | | 2 | | | | |
| Photonyl ® LS | | | | 2 | | | | | | | 2 |
| Panthenol | | | | | | 1.0 | | | | | |
| Bisabolol | | | | | | 0.2 | | | | | |
| Tocopherol/Tocopherylacetate | | | | | | 1.0 | | | | | |
| Magnesium sulfate × 7 water | | | | | | 1 | | | | | |
| Bentone ® 38 | | | | | | 1 | | | | | |
| Propylenecarbonate | | | | | | 0.5 | | | | | |
| Ethanol | | | | 8 | | 10 | | | | | |
| Butyleneglycol | 5 | 1 | | 3 | 3 | | | | 8 | 2 | 1 |
| Glycerin | | | 6 | 2 | | | 5 | 5 | | 3 | 5 |
| Water, preservative | | | | | | to 100, q.s. | | | | | |

TABLE 7

O/W care emulsions

| L = Lotion, C = Cream | 67 C | 68 C | 69 C | 70 L | 71 C | 72 L | 73 L | 74 C | 75 L | 77 C | 77 C |
|---|---|---|---|---|---|---|---|---|---|---|---|
| Eumulgin ® VL 75 | | | | | | 4 | | | | | |
| Dehymuls ® PGPH | | 2 | | | | | | | | | |
| Generol ® R | | | 1 | | | | | | | | |
| Eumulgin ® B2 | | | 0.8 | | | | | | | | |
| Tween ® 60 | | | | 1 | | | | | | | |
| Cutina ® E 24 | | | 0.6 | 2 | | | | | | | |
| Hostaphat ® KL 340 N | | | | | | | | 2 | | | |
| Lanette ® E | | | | | | | | | 1 | | |
| Amphisol ® K | | 0.5 | | | 1 | | | | | 1 | 0.5 |
| Sodium stearate | | | | | 0.5 | | | | | | |
| Emulgade ® PL 68/50 | | 2.5 | | | | | | | | 4 | |
| Tego ® Care CG | | | | | | | | | | | 2 |
| Tego ® Care 450 | | | | | | | | 5 | | | |
| Cutina ® MD | | 1 | | 6 | 5 | | 4 | | 6 | | |
| Lanette ® 14 | | | | 1 | | | | 2 | | | 4 |
| Lanette ® O | 4.5 | | 4 | | 1 | 2 | | | | | 2 |
| Novata ® AB | | 1 | | | | | | | | | 1 |
| Emery ® 1780 | | | | | 0.5 | 0.5 | | | | | |
| Lanolin, anhydrous, USP | | | | | | | 5 | | | | |
| Cetiol ® SB 45 | | | 1.5 | | | | 2 | | | | |
| Undecane or tridecane | 3 | 4 | 2 | 1 | 10 | 2 | 2 | 6 | 3 | 12 | 1 |
| Cegesoft ® C 17 | | | | | | | | | | | |
| Myritol ® PC | | | | | 5 | | | | | | |
| Myritol ® 331 | 2 | 5 | 5 | | | 6 | | 12 | | | |

TABLE 7-continued

O/W care emulsions

| L = Lotion, C = Cream | 67 C | 68 C | 69 C | 70 L | 71 C | 72 L | 73 L | 74 C | 75 L | 77 C | 77 C |
|---|---|---|---|---|---|---|---|---|---|---|---|
| Finsolv ® TN | | | 2 | | | 2 | | | 8 | | |
| Cetiol ® CC | 4 | 6 | | | | 4 | 4 | | | | 5 |
| Cetiol ® OE | | | | | | | | | 4 | 3 | |
| Dow Corning DC ® 245 | | | 2 | | 5 | 1 | | | | | |
| Dow Corning DC ® 2502 | | | | | 2 | 1 | | | | | |
| Prisorine ® 3758 | | | | | | 1 | | | | | |
| Silikonöl Wacker AK ® 350 | 0.5 | 0.5 | 0.5 | | | 1 | 4 | | | | |
| Cetiol ® 868 | | | | | 2 | | 4 | | | | |
| Cetiol ® J 600 | 2 | | 3 | | 3 | 2 | | | | 5 | |
| Ceraphyl ® 45 | | | | | | | 3 | | | | |
| Mineral oil | | | | 9 | | | | | | | |
| Cetiol ® SN | | | 5 | | | | | | | | |
| Cetiol ® B | | | | | | | | | | 2 | |
| Eutanol ® G | | 2 | | 3 | | | | | | | |
| Cetiol ® PGL | | | | | | | | | 5 | 5 | |
| Dry Flo ® Plus | 5 | | | | | | 1 | | | | |
| SFE 839 | 5 | | | | | | | | | | 2 |
| Almond oil | | | | | | | 1 | | | | |
| Insect Repellent ® 3535 | | 2 | 4 | | | 2 | | | | 3 | |
| N,N-Diethyl-m-toluamide | | 2 | | | | | | | | 3 | |
| Photonyl ® LS | 2 | 2 | | | | 2 | | | | | |
| Panthenol | | | | | | | 1 | | | | |
| Bisabolol | | | | | | | 0.2 | | | | |
| Tocopherol/Tocopherylacetate | | | | | | | 1 | | | | |
| Veegum ® ultra | | | | | | | | | 1 | | |
| Keltrol ® T | | | 0.4 | | | | | | 0.5 | | |
| Pemulen ® TR 2 | 0.3 | | | | | | | 0.3 | | | |
| Carbopol ® Ultrez 10 | | 0.3 | 0.3 | 0.2 | 0.2 | 0.2 | | | 0.1 | 0.3 | 0.2 |
| Ethanol | | | | | | | | | | 10 | |
| Butyleneglycol | | | | 4 | 3 | | 2 | 5 | 2 | | |
| Glycerin | 2 | 5 | 5 | | 3 | 3 | 2 | | 4 | | 3 |
| Water, preservative, NaOH | | | | | | to 100, q.s. pH 6.5-7.5 | | | | | |

TABLE 8

O/W care emulsions

| L = Lotion, C = Cream | 78 C | 79 C | 80 L | 81 C | 82 L | 83 C | 84 L | 85 L | 86 L | 87 L | 88 C |
|---|---|---|---|---|---|---|---|---|---|---|---|
| Eumulgin ® VL 75 | 4 | 3 | | | | | 1 | | | 2 | |
| Generol ® R | | | | | | 2 | | | | | |
| Eumulgin ® B2 | | | | | | 2 | | | 1 | | |
| Tween ® 60 | | | | | | | | | 1 | | |
| Cutina ® E 24 | | | | 2 | | | | | | | |
| Hostaphat ® KL 340 N | | | | | | | | | | | |
| Lanette ® E | 0.5 | | | | | | | | | 1 | |
| Amphisol ® K | 0.5 | 1 | | | | | 1 | 1 | | | |
| Sodium stearate | | | | | 1 | | | | | | |
| Emulgade ® PL 68/50 | | | 6 | | | | | 5 | | 4 | |
| Tego ® Care CG | | | | | | | | | | | |
| Tego ® Care 450 | | | | | | | | 4 | | | |
| Cutina ® MD | 3 | | 3 | 8 | 6 | 8 | | | | 4 | |
| Lanette ® 14 | | 2 | | | | | 2 | | | 1 | |
| Lanette ® O | 2 | | | 2 | | 3 | 1 | | 1 | 1 | 6 |
| Novata ® AB | | | | | | | | | | | |
| Emery ® 1780 | | | | | | | | | | | |
| Lanolin, anhydrous, USP | | | | | 4 | | | | | | |
| Cetiol ® SB 45 | | | | | | 2 | | | | | |
| Undecane or tridecane | 3 | 4 | 2 | 1 | 10 | 2 | 2 | 6 | 3 | 12 | 1 |
| Cegesoft ® C 17 | 4 | | | | | | | | | | |
| Myritol ® PC | 6 | | | | 5 | | | 5 | | | |
| Myritol ® 331 | 5 | | 5 | | | 7 | | | 10 | 3 | |
| Finsolv ® TN | | 5 | | | 5 | | 3 | 3 | | 1 | |
| Cetiol ® CC | | | | | | | | | | 2 | |
| Cetiol ® OE | | | | | 2 | | 2 | 5 | | | |
| Dow Corning DC ® 245 | | 2 | | 1 | | | | | 8 | 2 | |

TABLE 8-continued

O/W care emulsions

| L = Lotion, C = Cream | 78 C | 79 C | 80 L | 81 C | 82 L | 83 C | 84 L | 85 L | 86 L | 87 L | 88 C |
|---|---|---|---|---|---|---|---|---|---|---|---|
| Dow Corning DC ® 2502 | | 1 | | | 1 | | | | | | 3 |
| Prisorine ® 3758 | 3 | | | | | | | | | | 2 |
| Silikonöl Wacker AK ® 350 | | | | | 1 | | | | | | 1 |
| Cetiol ® 868 | | | 2 | | | | | | | | |
| Cetiol ® J 600 | | | 2 | | | | | | | | |
| Ceraphyl ® 45 | | | | | | | 3 | | | | |
| Cetiol ® SN | | | | | | | | | | | |
| Cetiol ® B | | | 5 | | | 5 | | 4 | | | 3 |
| Eutanol ® G | | 3 | 5 | | 5 | | | | | | |
| Cetiol ® PGL | | | | | | | | | 5 | 2 | |
| Dry Flo ® Plus | | 1 | | | | | | | | | 1 |
| SFE 839 | 1 | 1 | | | | | | | | | |
| Almond oil | | | | | | 2 | | | | | |
| Photonyl ® LS | | | | | | 2 | | | | | |
| Panthenol | | | | | | 1 | | | | | |
| Bisabolol | | | | | | 0.2 | | | | | |
| Tocopherol/Tocopherylacetate | | | | | | 1 | | | | | |
| Veegum ® Ultra | | | | | | | | | 1 | | |
| Keltrol ® T | | | | | | | | | 0.5 | | |
| Carbopol ® ETD 2001 | | 0.3 | | 0.3 | | 0.5 | 0.2 | 0.2 | | | |
| Pemulen ® TR 2 | | | 0.3 | | | 0.3 | | | | | 0.5 |
| Ethanol | | | 5 | | 8 | | | | | | 10 |
| Butylene glycol | 5 | | 2 | 3 | 3 | | | | | 8 | |
| Glycerin | 2 | 4 | 3 | 3 | | 7 | 5 | 3 | 5 | | |
| Water, preservative, NaOH | | | | | | to 100, q.s. (pH 6.5-7.5) | | | | | |

TABLE 9

Spray formulations

| S = Body spray, S* = Sun protection spray | 89 S | 90 S | 91 S | 92 S | 93 S | 94 S* | 95 S* | 96 S* | 97 S* | 98 S* | 99 S* |
|---|---|---|---|---|---|---|---|---|---|---|---|
| Emulgade ® SE-PF | 8.9 | | 7.5 | 7.5 | 4.3 | 9.8 | 8.2 | 9.9 | | | |
| Eumulgin ® B2 | 3.1 | | 3 | | | | | 4.2 | | | |
| Eumulgin ® B3 | | | | | | 4.2 | 3.3 | | | | |
| Eumulgin ® HRE 40 | | | | | 4.7 | | | | | | |
| Cutina ® E 24 | | 5.9 | | 4 | | | | | | | |
| Amphisol ® K | | | | | | | | | 1 | 1 | 1 |
| Eumulgin ® VL 75 | | | | | | | | | | | 2 |
| Emulgade ® PL 68/50 | | 0.5 | | | | | | | 2.5 | 1 | |
| Cutina ® MD | | 3.1 | | | | | | | | | |
| Antaron V 220 | | | | | | 1 | 1 | 1 | | 1 | 1 |
| Undecane or tridecane | 11 | 5 | 7 | 7 | 7 | 5 | 4 | 5 | 5 | 4 | 6 |
| Myritol ® PC | | | | | | | | | | | |
| Myritol ® 331 | | | 3 | 4 | 3 | 3 | 3 | 3 | | | |
| Finsolv ® TN | | | 4 | | | | | 8 | | | |
| Cetiol ® CC | 6 | | | 5 | 5 | 2 | 2 | 4 | | | |
| Cetiol ® OE | | | 5 | 5 | | 2 | | | | | |
| Dow Corning DC ® 244 | | | 4 | 4 | 5 | | | | | | |
| Cetiol ® 868 | | 3 | | | | | | | | | |
| Cetiol ® J 600 | | | | 2 | 2 | | | | | | |
| Mineral oil | | | 2 | | | | | | | | |
| Cetiol ® B | | | | | | | 2 | | | | |
| Eutanol ® G | 2 | | | 1 | | | | | | | |
| Photonyl ® LS | 2 | | | | | 2 | | | 2 | 2 | |
| Panthenol | | | | | | 1 | | | | | |
| Bisabolol | | | | | | 0.2 | | | | | |
| Tocopherol/Tocopherylacetat | | | | | | 1 | | | | | |
| Neo Heliopan ® Hydro (Na salt) | | | | | | 2 | | | 3 | | |
| Neo Heliopan AP (Na salt) | | | | | | 2 | 2 | 2 | | | 1 |
| Eusolex ® OCR | | | | | | | 2 | | | | 3 |
| Neo Heliopan ® BB | | | | | | | | | 1 | | |
| Neo Heliopan ® MBC | | | | | | 2 | 2 | 2 | | 1 | 1 |
| Neo Heliopan ® OS | | | | | | 5 | | | | | |
| Neo Heliopan ® AV | | | | | | 6 | 6 | 2 | | 7.5 | 2 |
| Uvinul ® T 150 | | | | | | 1 | 1 | 1 | | 1 | |

TABLE 9-continued

Spray formulations

| S = Body spray, S* = Sun protection spray | 89 S | 90 S | 91 S | 92 S | 93 S | 94 S* | 95 S* | 96 S* | 97 S* | 98 S* | 99 S* |
|---|---|---|---|---|---|---|---|---|---|---|---|
| Parsol ® 1789 | | | | | | 1 | | 1 | | 1 | |
| Z-Cote ® HP 1 | | | | | | | | | | 2 | 2 |
| Eusolex ® T 2000 | | | | | | | | | | 2 | 2 |
| Veegum ® Ultra | | | | | | | | | | | 1.5 |
| Laponite ® XLG | | | | | | | | | | 1.5 | |
| Keltrol ® T | | | | | | | | | | | 0.5 |
| Pemulen ® TR 2 | | | | | | | | | 0.2 | | |
| Insect Repellent ® 3535 | 1 | | | | | | | | | | |
| N,N-Diethyl-m-toluamide | | 1 | | | | | | | | | |
| Ethanol | | | | | | | | | | | |
| Butylene glycol | | | | | | 1 | | | | 2 | 1 |
| Glycerin | | | | | | 3 | 2 | 3 | 2 | | 3 |
| Water/preservative/NaOH | to 100/q.s./q.s | | | | | | | | | | |

APPENDIX

1) Abil® EM 90
INCI: Cetyl Dimethicone Copolyol
Manufacturer: Tego Cosmetics (Goldschmidt)
2) Amphisol® K
INCI: Potassium Cetyl Phosphate
Manufacturer: Hoffmann La Roche
3) Antaron® V 220
INCI: PVP/Eicosene Copolymer
Manufacturer: GAF General Aniline Firm Corp. (IPS-Global)
4) Antaron®V 216
INCI: PVP/Hexadecene Copolymer
Manufacturer: GAF General Aniline Firm Corp. (IPS-Global)
5) Arlacel® 83
INCI: Sorbitan Sesquioleate
Manufacturer Uniqema (ICI Surfactants)
6) Arlacel® P 135
INCI: PEG-30 Dipolyhydroxystearate
Manufacturer: Uniqema (ICI Surfactants)
7) Bentone® 38
INCI: Quaternium-18 Hectorite
Manufacturer: Rheox (Elementis Specialties)
8) Carbopol® 980
INCI: Carbomer
Manufacturer: Goodrich
9) Carbopol® 2984
INCI: Carbomer
Manufacturer Goodrich
10) Carbopol® ETD 2001
INCI: Carbomer
Manufacturer: BF Goodrich
11) Carbopol® Ultrez 10
INCI: Carbomer
Manufacturer Goodrich
12) Cegesoft® C 17
INCI: Myristyl Lactate
Manufacturer: Cognis Deutschland GmbH, Grünau
13) Ceraphyl®45
INCI: Diethylhexyl Malate
Manufacturer: International Specialty Products
14) Cetiol®868
INCI: Ethyhexyl Stearate
Manufacturer: Cognis Deuschland GmbH
15) Cetiol® A
INCI: Hexyl Laurate
Manufacturer: Cognis Deutschland GmbH
16) Cetiol®B
INCI: Butyl Adipate
Manufacturer: Cognis Deutschland GmbH (Henkel)
17) Cetiol® J 600
INCI: Oleyl Erucate
Manufacturer: Cognis Deutschland GmbH
18) Cetiol® OE
INCI: Dicaprylyl Ether
Manufacturer: Cognis Deutschland GmbH
19) Cetiol® PGL
INCI: Hexyldecanol, Hexyldecyl Laurate
Manufacturer: Cognis Deutschland GmbH
20) Cetiol® CC
INCI: Dicaprylyl Carbonate
Manufacturer: Cognis Deutschland GmbH
21) Cetiol® SB 45
INCI: Shea Butter Butyrospermum Parkii (Linne)
Manufacturer: Cognis Deutschland GmbH
22) Cetiol® SN
INCI: Cetearyl Isononanoate
Manufacturer: Cognis Deutschland GmbH (Henkel)
23) Cutina® E 24
INCI: PEG-20 Glyceryl Stearate
Manufacturer: Cognis Deutschland GmbH
24) Cutina® MD
INCI: Glyceryl Stearate
Manufacturer Cognis Deutschland GmbH
25) Dehymuls® FCE
INCI: Dicocoyl Pentaerythrityl Distearyl Citrate
Manufacturer: Cognis Deutschland GmbH
26) Dehymuls® HRE 7
INCI: PEG-7 Hydrogenated Castor Oil
Manufacturer: Cognis Deutschland GmbH
27) Dehymuls® PGPH
INCI: Polyglyceryl-2 Dipolyhydroxystearate
Manufacturer Cognis Deutschland GmbH
28) Dow Corning®244 Fluid
INCI: Cyclomethicone
Manufacturer: Dow Corning
29) Dow Corning® 245 Fluid
INCI: Cyclopentasiloxane Cyclomethicone
Manufacturer: Dow Corning 30) Dow Corning® 2502
INCI: Cetyl Dimethicone
Manufacturer: Dow Corning
31) Dry® Flo Plus
INCI: Aluminium Starch Octenylsuccinate
Manufacturer National Starch
32) Elfacos® ST 37
INCI: PEG-22 Dodecyl Glycol Copolymer
Manufacturer: Akzo-Nobel
33) Elfacos® ST 9
INCI: PEG45 Dodecyl Glycol Copolymer
Manufacturer: Akzo-Nobel
34) Emery® 1780
INCI: Lanolin Alcohol
Manufacturer: Cognis Corporation (Emery)
35) Emulgade® PL 68/50
INCI: Cetearyl Glucoside, Ceteayl Alcohol
Manufacturer: Cognis Deutschland GmbH
36) Emulgade® SE-PF
INCI: Glyceryl Stearate, Ceteareth-20, Ceteareth-12, Cetearyl Alcohol, Cetyl Palmitate
Manufacturer Cognis Deutschland GmbH
37) Eumulgin® B 2
INCI: Ceteareth-20
Manufacturer: Cognis Deutschland GmbH
38) Eumulgin® VL 75
INCI: Lauryl Glucoside (and) Polyglyoeryl-2 Dipolyhydroxystearate (and) Glycerin
Manufacturer: Cognis Deutschland GmbH
39) Eusolex® OCR
INCI: Octocrylene
Manufacturer: Merck
40) Eusolex® T 2000
INCI: Titanium Dioxide, Alumina, Simethicone
Manufacturer Rona (Merck)
41) Eutanol®G
INCI: Octyldodecanol
Manufacturer: Cognis Deutschland GmbH
42) Eutanol®G 16
INCI: Hexyldecanol
Manufacturer: Cognis Deutschland GmbH
43) Eutanol® G 16 S
INCI: Hexyldecyl Stearate
Manufacturer: Cognis Deutschland GmbH
44) Finsolv® TN
INCI: C 12/15 Alkyl Benzoate
Manufacturer: Findex (Nordmann/Rassmann)
45) Generol® R
INCI: Brassica Campestris (Rapseed) Sterols
Manufacturer: Cognis Deutschland GmbH
46) Glucate® DO
INCI: Methyl Glucose Dioleate
Manufacturer: NRC Nordmann/Rassmann
47) Hostaphat® KL 340 N
INCI: Trilaureth-4 Phosphate
Manufacturer: Clariant
48) Isolan® PDI
INCI: Dilsostearoyl Polyglyceryl-3-Diisostearate
Manufacturer: Goldschmidt AG
49) Keltol® T
INCI: Xanthan Gum
Manufacturer: CP Kelco
50) Lameform® TGI
INCI: Polyglyoeryl-3 Diisostearate
Manufacturer: Cognis Deutschland GmbH
51) Lanette® 14
INCI: Myristyl Alcohol
Manufacturer: Cognis Deutschland GmbH
52) Lanette® E
INCI: Sodium Cetearyl Sulfate
Manufacturer: Cognis Deutschland GmbH
53) Lanette® O
INCI: Cetearyl Alcohol
Manufacturer: Cognis Deutschland GmbH
54) Monomuls® 90-0-18
INCI: Glyoeryl Oleate
Manufacturer Cognis Deutschland GmbH
55) Myrj® 51
INCI: PEG-30-Sterate
Manufacturer: Uniqema
56) Myrritol® 331
INCI: Cocoglycerides
Manufacturer Cognis Deutschland GmbH
57) Myrritol® PC
INCI: Propylene Glycol Dicaprylate/Dicaprate
Manufacturer: Cognis Deutschland GmbH
58) Neo Heliopan® 303
INCI: Octocrylene
Manufacturer Haarmann & Reimer
59) Neo Heliopan® AP
INCI: Disodium Phenyl Dibenzimidazole Tetrasulfonate
Manufacturer: Haarmann & Reimer
60) Neo Heliopan® AV
INCI: Ethylhexyl Methoxycinnamate
Manufacturer: Haarmann & Reimer
61) Neo Heliopan® BB
INCI: Benzophenone-3
Manufacturer: Haarmann & Reimer
62) Neo Heliopan® E 1000
INCI: Isoamyl-p-Methoxycinnamate
Manufacturer: Haarmann & Reimer
63) Neo Heliopan® Hydro (Na-Salz)
INCI: Phenylbenzimidazole Sulfonic Acid
Manufacturer Haarmann & Reimer
64) Neo Heliopan® MBC
INCI: 4-Methybenzylidene Camphor
Manufacturer: Haarmann & Reimer
65) Neo Heliopan® OS
INCI: Ethylhexyl Salicylate
Manufacturer: Haarmann & Reimer
66) Novata® AB
INCI: Cocoglycerides
Manufacturer: Cognis Deutschland GmbH
67) Parsol® 1789
INCI. Butyl Methoxydibenzoylmethane
Manufacturer: Hoffmann-La Roche (Givaudan)
68) Pemulen® TR-2
INCI: Acrylates/C10-30 Alkylacrylate Crosspolymer
Manufacturer: Goodrich
69) Photonyl® LS
INCI: Arginine, Disodium Adenosine Triphosphate, Mannitol, Pyridoxine HCL, Phenylalanine, Tyrosine
Manufacturer: Laboratoires Serobiologiques (Cognis)
70) Prisorine® ISAC 3505
INCI: Isostearic Acid
Manufacturer: Uniqema
71) Prisorine® 3758
INCI: Hydrogenated Polyisobutene
Manufacturer: Uniqema
72) Ravecarb® 106
Polycarbonatdiol
Manufacturer: Enichem 73) SFE® 839
INCI: Cyclopentasiloxane and Dimethicone/Vinyl Dimethicone Crosspolymer
Manufacturer: GE Silicones
74) Silikonöl Wacker AK® 350
INCI: Dimethicone
Manufacturer: Wacker
75) Squatol® S
INCI: Hydrogenated Poyisobutene
Manufacturer: LCW (7-9 rue de l'Industrie 95310 St-Ouen l'Aumone France)
76) Tego® Care 450
INCI: Polyglyceryl-3 Methylglucose Distearate
Manufacturer Tego Cosmetics (Goldschmidt)
71) Tego® Care CG 90
INCI: Cetearyl Glucoside
Manufacturer: Goldschmidt
78) Tween® 60
INCI: Polysorbate 60
Manufacturer: Uniqema (ICI Surfactants)
79) Uvinul® T 150
INCI: Octyl Triazone
Manufacturer: BASF
80) Veegum® Ultra
INCI: Magnesium Aluminium Silicate
Manufacturer: Vanderbilt
81) Z-Cote® HP 1
INCI: Zinc Oxide, Dimethicone
Manufacturer: BASF

What is claimed is:

1. A process for the production of linear saturated alkanes from one or more primary alcohols, wherein the carbon chain of the one or more primary alcohols has one carbon atom more than the alkane, comprising
conducting reductive dehydroxymethylation of one or more primary fatty alcohols containing 8 to 24 carbon atoms, at a temperature ranging from 100 to 240° C. and pressures from 1 to 50 bar in the presence of hydrogen and a catalyst, wherein the catalyst comprises nickel, and wherein the catalyst is used in quantities of about 0.1 to about 1% by weight, based on the quantity of fatty alcohol used; and
removing water formed during the reaction.

2. The process according to claim 1, wherein the reaction is carried out at a temperature ranging from 180 to 240° C.

3. The process according to claim 1, wherein the reaction is carried out at a temperature ranging from 200 to 240° C.

4. The process according to claim 1, wherein the reaction is carried out at a temperature ranging from 220 to 240° C.

5. The process according to claim 1, wherein the reaction is carried out under pressures from 2 to 50 bar.

6. The process according to claim 1, wherein the reaction is carried out under pressures from 10 to 20 bar.

7. The process according to claim 1, wherein the catalyst is used in quantities of 0.2 to 1% by weight, based on the quantity of fatty alcohol used.

8. The process according to claim 1, wherein the one or more primary fatty alcohols correspond to the general formula R—OH, wherein R is a saturated linear alkyl group containing 8 to 18 carbon atoms.

9. The process according to claim 1, wherein the one or more primary fatty alcohols correspond to the general formula R—OH, wherein R is a saturated linear alkyl group containing 10 to 16 carbon atoms.

10. The process according to claim 1, wherein the one or more primary fatty alcohols correspond to the general formula R—OH, wherein R is a saturated linear alkyl group containing 12 to 16 carbon atoms.

11. The process according to claim 1, wherein the one or more primary fatty alcohols contains an even number of carbon atoms.

12. The process according to claim 1, wherein a mixture of two or more primary alcohols is used.

13. The process according to claim 1, further comprising the step of purifying the product obtained by the reaction.

14. A linear saturated alkane obtained by the process according to claim 1, incorporated into a cosmetic preparation.

15. The process according to claim 1, wherein the water is removed continuously during the process.

16. The process according to claim 1, wherein the catalyst comprises 63 wt % nickel, 16 wt %, amorphous silica, and 8 wt % magnesium oxide.

17. The process according to claim 16, wherein the primary fatty alcohol is 1-tetradecanol and the linear saturated alkane is tridecane.

18. The process according to claim 16, wherein the primary fatty alcohol is 1-dodecanol and the linear saturated alkane is undecane.

* * * * *